United States Patent
Yang et al.

(10) Patent No.: US 7,138,445 B2
(45) Date of Patent: Nov. 21, 2006

(54) FLAME RETARDANT THERMOPLASTIC RESIN COMPOSITION

(75) Inventors: Jae Ho Yang, Geonggi-Do (KR); Sang Hyun Hong, Gyeonggi-Do (KR); Gyu Chul Lee, Gyeonggi-Do (KR); Bok Nam Jang, Seoul (KR); Young Gil Jang, Seoul (KR); Sung Hee Ahn, Seoul (KR); Su Hak Bae, Seoul (KR); Jong-Cheol Lim, Kyongki-Do (KR); Kyung-Hoon Seo, Seoul (KR); Sam-Joo Yang, Kyongki-Do (KR)

(73) Assignee: Cheil Industries Inc., Kyungsangbuk-do (KR)

( * ) Notice: Subject to any disclaimer, the term of this patent is extended or adjusted under 35 U.S.C. 154(b) by 0 days.

(21) Appl. No.: 10/731,757

(22) Filed: Dec. 8, 2003

(65) Prior Publication Data

US 2004/0122139 A1 Jun. 24, 2004

Related U.S. Application Data

(63) Continuation-in-part of application No. PCT/KR01/02261, filed on Dec. 26, 2001, which is a continuation-in-part of application No. PCT/KR01/02262, filed on Dec. 26, 2001, which is a continuation-in-part of application No. 10/223,450, filed on Aug. 19, 2002, now Pat. No. 6,900,256, which is a continuation of application No. 09/997,781, filed on Nov. 28, 2001, now Pat. No. 6,576,161, which is a continuation-in-part of application No. 09/752,814, filed on Dec. 29, 2000, now Pat. No. 6,437,029.

(30) Foreign Application Priority Data

| Oct. 31, 2000 | (KR) | 2000-64325 |
| Nov. 28, 2000 | (KR) | 2000-71314 |
| Jun. 8, 2001 | (KR) | 2001-31956 |
| Jun. 8, 2001 | (KR) | 2001-31959 |

(51) Int. Cl.
*C08K 5/5399* (2006.01)
*C08L 25/00* (2006.01)
*C08L 69/00* (2006.01)
*C08L 71/12* (2006.01)

(52) U.S. Cl. .......... 523/451; 524/96; 524/97; 525/65; 525/67

(58) Field of Classification Search ........ 523/451; 524/96, 97; 525/65, 67
See application file for complete search history.

(56) References Cited

U.S. PATENT DOCUMENTS

| 4,062,909 | A | * | 12/1977 | Morgan et al. ............ 558/157 |
| 4,883,835 | A | | 11/1989 | Buysch et al. ............. 524/504 |
| 4,983,658 | A | | 1/1991 | Kress et al. ................ 524/141 |
| 5,731,390 | A | * | 3/1998 | Helmond .................... 525/438 |
| 5,905,122 | A | * | 5/1999 | Ohtsuka et al. ............ 525/465 |
| 6,437,029 | B1 | | 8/2002 | Lim et al. .................... 524/97 |
| 6,576,161 | B1 | | 6/2003 | Lim et al. .................. 252/609 |
| 6,630,524 | B1 | | 10/2003 | Lim et al. .................. 524/100 |
| 6,797,754 | B1 | | 9/2004 | Yang et al. |
| 2004/0192814 | A1 | * | 9/2004 | Yang et al. ................ 524/115 |
| 2004/0198877 | A1 | * | 10/2004 | Yang et al. ................ 524/115 |

FOREIGN PATENT DOCUMENTS

| EP | 0 728 811 A2 | 8/1996 |
| JP | 7-76649 | 3/1995 |
| JP | 8-208884 | 9/1996 |
| KR | 1994-0014647 | 7/1994 |

OTHER PUBLICATIONS

Abstract of Korean Patent Application Laid-open No. 94-14647, Jul. 19, 1994.
Abstract of Japanese Patent Laid-open No. 8-208884, Aug. 13, 1996.
Abstract of Japanese Patent Laid-open No. 7-76649, Mar. 2, 1995.
Abstract of EP0936244, Aug. 18, 1999.

* cited by examiner

*Primary Examiner*—David J. Buttner
(74) *Attorney, Agent, or Firm*—Maria Parrish Tungol

(57) ABSTRACT

The present invention relates to a flame retardant thermoplastic resin composition that contains a phenol resin derivative having good char formability, regardless of the base resin. A flame retardant thermoplastic resin composition according to the present invention comprises (A) 100 parts by weight of a thermoplastic resin as a base resin, (B) about 0.1~100 parts by weight of a phenol resin derivative, and (C) about 0.1~50 parts by weight of a phosphoric acid ester morpholide compound or a mixture of phosphoric acid ester morpholide compounds. Another flame retardant thermoplastic resin composition according to the present invention comprises (A) 100 parts by weight of a thermoplastic resin as a base resin, (B) about 0.1~100 parts by weight of polyphenylene ether, (C) about 0.1~100 parts by weight of a phenol resin derivative, and (D) about 0.1~50 parts by weight of a phosphoric acid ester morpholide compound or a mixture of phosphoric acid ester morpholide compounds. The thermoplastic resin composition containing polyphenylene ether resin may also contain up to 5.0 parts by weight of an anti-dripping agent based on 100 parts by weight of the base resin.

15 Claims, No Drawings

FLAME RETARDANT THERMOPLASTIC RESIN COMPOSITION

This application is a continuation-in-part of International Application No. PCT/KR01/02261 filed Dec. 26, 2001, published in English under PCT Article 21(2) and now abandoned and a continuation-in-part of International Application No. PCT/KR01/02262 filed Dec. 26, 2001, published in English under PCT Article 21(2) and now abandoned. This application is also a continuation-in-part of Ser. No. 10/223,450 filed Aug. 19, 2002, now U.S. Pat. No. 6,900,256, which is a continuation of Ser. No. 09/997,781, filed Nov. 28, 2001, now U.S. Pat. No. 6,576,161, which is a continuation-in-part of Ser. No. 09/752,814 filed Dec. 29, 2000, now U.S. Pat. No. 6,437,029.

FIELD OF THE INVENTION

The present invention relates to a thermoplastic resin composition with good flame retardancy. More particularly, the present invention relates to a flame retardant thermoplastic resin composition that contains a phenol resin derivative having good char formability, regardless of the base resin.

BACKGROUND OF THE INVENTION

To improve flame retardancy of a thermoplastic resin composition is a major target to the research and development of the resin for a long time. It has been known the best method of using a halogen compound to prepare a flame retardant thermoplastic resin composition. U.S. Pat. Nos. 4,983,658 and 4,883,835 disclose thermoplastic resin compositions using a halogen compound as a flame retardant. The thermoplastic resin composition using a halogen compound shows good flame retardancy regardless of the base resin. However, the disadvantages could be observed that the halogen-containing compound results in the corrosion of the mold itself by the hydrogen halide gases released during the molding process and is fatally harmful due to the toxic gases liberated in case of fire. Therefore, halogen-free flame retardants have become a major concern in this field.

The representative halogen-free flame retardant is a phosphorous flame retardant nowadays. The phosphorous compound is superior to the halogen compound in corrosion of apparatus and toxic gas liberation. However, the phosphorous compound cannot provide better flame retardancy than the halogen compound, and, if more amount of the phosphorous compound is used to improve flame retardancy, the heat resistance is deteriorated. Furthermore, base resins are limited when the phosphorous compound is used as a flame retardant.

Another method to improve flame retardancy of a thermoplastic resin composition is add a material with good char formability to the base resin with poor char formability to form char film during combustion. The char film blocks transporting of oxygen, heat, and other fuel gases which could accelerate combustion of the resin.

As a phenol resin has a good char formability, it has been targeted to conduct a research of the flame retardant thermoplastic resin composition. However, the phenol resin has disadvantages that the intensity of the char film is not so strong, the phenol resin has a poor compatibility with other resin due to polarity of the resin, and a color change problem occurs because of weak weatherability.

Accordingly, the present inventors have developed a flame retardant thermoplastic resin composition that employs a phenol resin derivative which overcome the shortcomings above of the phenol resin. In the flame retardant thermoplastic resin composition according to the present invention, the phenol resin derivative solves the color change problem due to use of phenol resin and improves compatibility with other polymer resins. The phenol resin derivative provides the flame retardant thermoplastic resin composition with good char formability. The thermoplastic resin composition according to the present invention have good weatherability against ultraviolet light, good compatibility with other polymer resins, do not cause corrosion of the mold apparatus by the hydrogen halide gases released during the molding process, and do not liberate toxic gases in case of fire.

The present invention also includes flame retardant thermoplastic resin compositions that employs a phenol resin derivative together with a polyphenylene ether resin to provide a synergistic effect. These thermoplastic resin compositions show better flame retardancy than resin compositions which use a phenol resin derivative without the polyphenylene ether resin and resin compositions which use polyphenylene ether resin in the absence of the phenol resin derivative.

SUMMARY OF THE INVENTION

A flame retardant thermoplastic resin composition according to the present invention comprises (A) 100 parts by weight of a thermoplastic resin as a base resin, (B) about 0.1~100 parts by weight of a phenol resin derivative, and (C) about 1~50 parts by weight of a phosphoric acid ester morpholide compound or a mixture of phosphoric acid ester morpholide compounds. Another flame retardant thermoplastic resin composition according to the present invention comprises (A) 100 parts by weight of a thermoplastic resin as a base resin, (B) about 0.1~100 parts by weight of polyphenylene ether, (C) about 0.1~100 parts by weight of a phenol resin derivative, and (D) about 0.1~50 parts by weight of a phosphoric acid ester morpholide compound or a mixture of phosphoric acid ester morpholide compounds. The thermoplastic resin composition containing polyphenylene ether may also contain up to 5.0 parts by weight of an anti-dripping agent based on 100 parts by weight of the base resin.

DETAILED DESCRIPTION OF THE INVENTION (A) Thermoplastic Resin (Base Resin)

Any thermoplastic resin can be used as a base resin in the present invention. In case of using a phosphorous compound as a flame retardant, the base resin is limited because it is difficult to obtain a sufficient flame retardancy.

In a preferred embodiment of the present invention, both a phenol resin derivative and a polyphenylene ether resin are employed, so a thermoplastic resin with no or poor char formability can be used as a base resin, resulting in sufficient flame retardancy.

The examples of the thermoplastic resin as base resin include polyacrylonitrile-butadiene-styrene copolymer (ABS resin), rubber modified polystyrene resin (HIPS), acrylonitrile-styrene-acrylate copolymer (ASA resin), methacrylate-butadiene-styrene copolymer (MBS resin), acrylonitrile-ethacrylate-styrene copolymer (AES resin), polycarbonate (PC), polyethylene (PE), polypropylene (PP), polyethylene terephthalate (PET), polybutylene terephthalate (PBT), polyvinyl chloride (PVC), polymethyl methacrylate (PMMA), polyamide (PA), and a copolymer thereof and an alloy thereof.

(B) Phenol Resin Derivative

When a phenol resin is used in a thermoplastic resin composition to improve flame retardancy, the phenol resin has disadvantages that the intensity of the char film is not so strong, the phenol resin has a poor compatibility with other resin due to polarity of the resin, and a color change problem occurs because of weak weatherability against ultraviolet. A phenol resin derivative is used to overcome the shortcomings of a phenol resin. The phenol resin derivative has good compatibility with other polymer resins to be used. The phenol resin derivative is used to provide the base resin with good char formability so as to improve flame retardancy, which has a chemical structure represented by the following Formula (I):

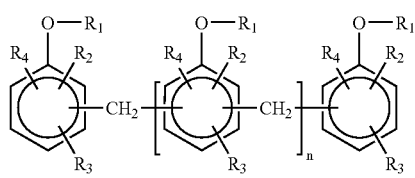

where $R_1$ is alkyl of $C_{1-34}$; aryl; alkyl-substituted aryl; O-, N-, P- or S-containing alkyl; O-, N-, P- or S-containing aryl; or O-, N-, P- or S-containing alkyl-substituted aryl; $R_2$, $R_3$, and $R_4$ are hydrogen, alkyl of $C_{1-34}$; aryl; alkyl-substituted aryl; O-, N-, P- or S-containing alkyl; O-, N-, P- or S-containing aryl; or O-, N-, P- or S-containing alkyl-substituted aryl; and n is an integer of 1 to 10,000, preferably 1 to 300 considering mechanical properties and processability.

During combustion, the phenol resin derivative prevents the combusted gases from flowing out by forming char film and oxygen or air from flowing in, functioning as a flame retardant additive. The phenol resin derivative overcomes disadvantages of phenol resin when the phenol resin is used in a thermoplastic resin composition, which are weak intensity of the char film, poor compatibility with other resin due to polarity of the phenol resin, and a color change problem due to weak weatherability.

The preferable examples of the phenol resin derivative include o-cresol novolak epoxy resin and phenol epoxy resin. The phenol resin derivatives are used in single or in mixture.

The phenol resin derivative may be used in the amount of about 0.01 to 100 parts by weight based on 100 parts by weight of the base resin.

(C) Phosphorous Compound

The phosphorous compound usable in the present invention include a phosphoric acid ester compound, a phosphoamidate compound, an oxaphosphorane compound, a carboxy phosphinic acid compound, phosphoric acid ester morpholide compound and a phosphazene compound. The phosphorous compounds are used in single or in combination. The phosphorous compound may be used in the amount of about 1 to 50 parts by weight based on 100 parts by weight of the base resin. The phosphorous compounds are described in detail as follow:

Phosphoric Acid Ester Compound and Phosphoamidate Compound: The phosphoric acid ester compound and phosphoamidate compound are represented by the following chemical Formula (II):

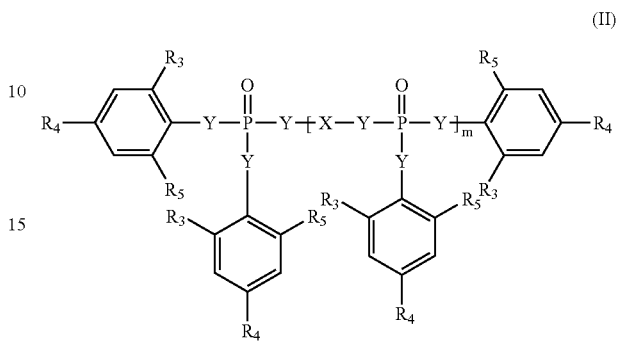

where $R_3$, $R_4$ and $R_5$ are hydrogen or alkyl of $C_{1-4}$, X is aryl of $C_{6-20}$ or aryl of alkyl-substituted $C_{6-20}$ that are derivatives from dialcohol such as resorcinol, hydroquinol, bisphenol-A and bisphenol-S, Y is oxygen or nitrogen, and m is in the range of 0 to 4.

If m is 0 in Formula (II), the compounds may be triphenyl phosphate, tricresyl phosphate, trixylenyl phosphate, tri(2, 6-dimethylphenyl)phosphate, tri(2,4,6-trimethylphenyl) phosphate, tri(2,4-ditertiarybutylphenyl)phosphate, tri(2,6-ditertiarybutylphenyl)phosphate and the like, and if m is 1, the compounds may be resorcinolbis(diphenyl)phosphate, resorcinolbis(2,6-dimethylphenyl)phosphate, resorcinolbis (2,4-ditertiary butylphenyl)phosphate, phosphate hydroquinol(2,6-dimethylphenyl)phosphate, hydroquinol(2,4-ditertiarybutylphenyl) and the like. The phosphorous compounds are used in single or in combination.

Oxaphospholane Compound: The oxaphospholane compound is represented by the following chemical Formula (III):

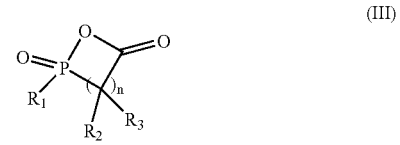

where $R_1$ is hydrogen, alkyl of $C_{1-6}$, or aryl of $C_{6-15}$, $R_2$ and $R_3$ are hydrogen or alkyl of $C_{1-6}$, and n is in the range of 1 to 3.

The preferable examples of the oxaphospholane compound are 2-methyl-2, 5-dioxo-1 -oxa-2-phospholane and 2-phenyl-2,5 -dioxo-1-oxa-2-phospholane. The oxaphospholane compounds are used in single or in combination.

The oxaphospholane compounds are known in the art as in U.S. Pat. No. 5,334,769, herein incorporated by reference. Rubber modified styrene-containing resin composition containing oxaphospholane compounds flame retardants are disclose in commonly assigned Ser. No. 10231,448, now U.S. Pat. No. 6,900,256, herein incorporated by reference.

Carboxy Phosphinic Acid Compound: The carboxy phosphinic acid compound is represented by the following chemical Formula (IV):

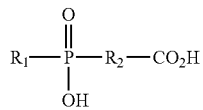

(IV)

where $R_1$ is hydrogen, alkyl of $C_{1-12}$, aryl of $C_{6-10}$, or alkyl-substituted aryl of $C_{7-15}$, $R_2$ is alkylene of $C_{1-12}$, ring type alkylene of $C_{1-12}$, aryl of $C_{6-12}$, or alkyl-substituted aryl of $C_{6-12}$.

The preferable examples of the carboxy phosphinic acid compound are 2-carboxy-ethyl-methyl-phosphinic acid, 2-carboxy-ethyl-phenyl-phosphinic acid, and 2-carboxy-methyl-phenyl-phosphinic acid. The carboxy phosphinic acid compounds are used in single or in combination.

Phosphoric Acid Ester Morpholide Compound: The phosphoric acid ester morpholide compound is represented by the following chemical Formula (V):

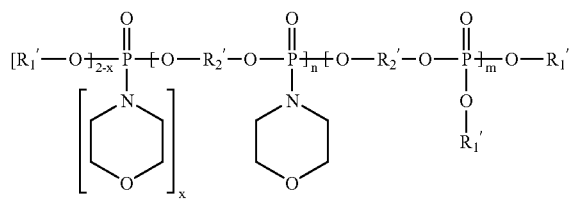

(V)

where $R'_2$ is a $C_{6-20}$ aryl group or an alkyl-substituted C620 aryl group, $R'_2$ is a $C_{6-30}$ aryl group or an alkyl-substituted $C_{6-30}$ aryl group, x is 1 or 2, and n and m are number average degree of polymerization and n+m is 0 to 5. In Formula (V), preferably $R'_1$ is a phenyl group or an alkyl-substituted phenyl group where the alkyl is methyl, ethyl, isopropyl, t-butyl, isobutyl, isoamyl or t-amyl, preferably methyl, ethyl, isopropyl or t-butyl, and $R'_2$ means preferably a $C_{6-30}$ aryl group or an alkyl-substituted $C_{6-30}$ aryl group which is a derivative from resorcinol, hydroquinone or bisphenol-A.

The phosphoric acid ester morpholide compounds are used in single or in combination. The phosphoric acid ester morpholide compounds and the method of their preparation is disclosed in U.S. Pat. No. 6,576,161, herein incorporated by reference. Other resin compositions containing morpholide compounds as flame retardants are disclosed in U.S. Pat. No. 6,437,029 and Ser. No. 01/223,450, both herein incorporated by reference.

Phosphazene Compound: The linear phosphazene compound is represented by the following chemical Formula (VI) and the cyclic phosphazene compound is represented by the following chemical Formula (VII):

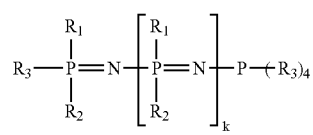

(VI)

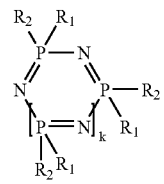

(VII)

where $R_1$, $R_2$, and $R_3$ are independently alkyl, aryl, alkyl substituted aryl, aralkyl, alkoxy, aryloxy, amino or hydroxyl, and k is an integer from 0 to 10. The alkoxy and aryloxy groups may be substituted with alkyl, aryl, amino, hydroxyl, nitrile, nitro, aryl with hydroxy, and the like.

Flame retardant polycarbonate compositions containing phosphazene flame retardants are disclosed in U.S. Pat. No. 6,630,524, herein incorporated by reference.

Other additives may be used in the thermoplastic resin composition of the present invention. The additives include an impact modifier, a heat stabilizer, an oxidation inhibitor, a light stabilizer, and an inorganic filler such as talc, silica, mica, glass fiber, an organic or inorganic pigment and/or dye. The additives are employed up to about 50 parts by weight as per 100 parts by weight of the base resin.

It has also been discovered that compositions containing thermoplastic resin (A) as base resin, phenol resin derivative (B), and phosphorous compound (D) together with a polyphenylene ether resin (B2) show better flame retardance compared to compositions which do not include (B2) and compositions which contain the polyphenylene ether resin (B2) without phenol resin derivative (B).

(B) Polyphenylene Ether (PPE)

The polyphenylene ether in the present invention functions to improve char formability of the thermoplastic resin composition during combustion along with the phenol resin derivative.

As examples of the polyphenylene ether resin, poly(2,6-dimethyl-1,4-phenylene)ether, poly(2,6-diethyl-1,4-phenylene)ether, poly(2,6-dipropyl-1,4-phenylene)ether, poly(2-methyl-6-ethyl-1,4-phenylene)ether, poly(2-methyl-6-propyl-1,4-phenylene)ether, poly(2-ethyl-6-propyl-1,4-phenylene)ether, poly(2,6-diphenyl-1,4-phenylene)ether, copolymer of poly(2,6-dimethyl-1,4-phenylene)ether and poly(2,3,6-trimethyl-1,4-phenylene)ether, and copolymer of poly(2,6-dimethyl-1,4-pheylene)ether and poly(2,3,5-triethyl-1,4-phenylene)ether can be used. Preferably, copolymer of poly(2,6-dimethyl-1,4-phenylene)ether and poly(2,3,6-trimethyl-1,4-phenylene)ether, and poly(2,6-dimethyl-1,4-phenylene)ether are preferably used, more preferably poly(2,6-dimethyl-1,4-phenylene)ether is used.

The degree of polymerization of polyphenylene ether is not limited specifically, but considering heat-stability or processability of the resin composition, it is preferable that the viscosity of polypheylene ether is in the range of about 0.1 to 0.8 measured in chloroform solvent at 25° C.

The polyphenylene ether resin is employed in the present invention to give a synergy effect with the phenol resin derivative that will be described below.

The polyphenylene ether may be used in the amount of about 0.01 to 100 parts by weight based on 100 parts by weight of the base resin.

In the compositions containing polyphenylene ether resin, the phosphorous compound (D) may be used in the amount of about 0.1 to 50 parts by weight based on 100 parts by weight of the base resin. The resin composition may also contain up to 5.0 parts by weight of an anti-dripping agent based on 100 parts by weight of the base resin. By using anti-dripping agent, the amounts of the flame retardant and/or char-forming agent can be reduced. The anti-dripping agent is used to prevent the melt resin from dripping during combustion. A fluoride resin is preferably used as an anti-dripping agent.

The fluoride resin form a fibrillar network with the base resin and other resins during extrusion, which will reduce the flow viscosity of the melt resin and increase shrinkage to prevent dripping. The preferable examples of the fluoride resin include polytetrafluoroethylene, polyvinylidenefluoride, copolymer of polytetrafluoroethylene and polyvinylidenefluoride, copolymer of polytetrafluoroethylene and fluoroalkylvinylether, and copolymer of polytetrafluoroethylene and hexafluoropropylene. Polytetrafluoroethylene may be used more preferably. The fluoride resin compounds are used in single or in combination.

Other additives may be used in these thermoplastic resin compositions include an impact modifier, a heat stabilizer, an oxidation inhibitor, a light stabilizer, and an inorganic filler such as talc, silica, mica, glass fiber, an organic or inorganic pigment and/or dye. The additives are employed up to about 50 parts by weight as per 100 parts by weight of the base resin.

The invention may be better understood by reference to the following examples which are intended for the purpose of illustration and are not to be construed as limiting the scope of the present invention, which is defined in the claims appended hereto. In the following examples, all parts and percentage are by weight unless otherwise indicated.

EXAMPLES

The components to prepare flame retardant thermoplastic resin compositions in Examples 1~12 and Comparative Examples 1~6 are as follows:

(A) Thermoplastic Resin (Base Resin)

(A$_1$) High Impact Polystyrene (HIPS)

The high impact polystyrene was prepared through a conventional process, having 9% by weight of rubber content, 1.5 μm of average rubber particle size, and 220,000 of weight average molecular weight.

(A$_2$) SAN Graft Copolymer 50 parts of butadiene rubber latex powder, 36 parts of styrene, 14 parts of acrylonitrile and 150 parts of deionized water were mixed. To the mixture, 1.0 parts of potassium oleate, 0.4 parts of cumenhydroperoxide, 0.2 parts of mercaptan-containing chain transfer agent, 0.4 parts of glucose, 0.01 parts of iron sulfate hydroxide and 0.3 parts of pyrophosphate sodium salt were added. The blend was kept at 75? for 5 hours to obtain ABS latex. To the ABS latex, 0.4 parts of sulfuric acid was added, coagulated and dried to obtain styrene-containing graft copolymer resin (g-ABS) in powder form.

(A$_3$) SAN Copolymer 75 parts of styrene, 25 parts of acrylonitrile, 120 parts of deionized water, 0.15 parts of azobisisobutylonitrile (AIBN) were blended. To the blend, 0.4 parts of tricalciumphosphate and 0.2 parts of mercaptan-containing chain transfer agent were added. The resultant solution was heated to 80? for 90 minutes and kept for 180 minutes. The resultant was washed, dehydrated and dried. Styrene-acrylonitrile copolymer (SAN) was obtained.

(A$_4$) Polycarbonate Resin

Polycarbonate of linear bisphenol-A type with a weight average molecular weight of 25,000 was used.

(B) Phenol Resin Derivative (B$_1$) The phenol resin derivative by Kukdo Chemical Co. of Korea (product name: YDCN-500-7P) was used, being represented by the following Formula (VIII):

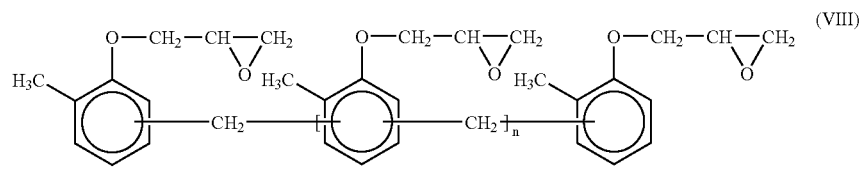

where n has an average value of 2.3.

(B$_2$) Novolak resin of 50 g with a softening point of 85° C., 200 g of benzyl chloride, and 150 g of isopropanol were dissolved in 20 ml of water, and the resulting solution was heated to 70° C. With agitation, 100 g of 20% NaOH was added to the solution over 1 hour. After reaction for more two hours, the solution was cooled to room temperature. The organic layer was separated from the water layer, and washed with distilled water several times. The separated organic layer was vacuum-distilled to remove benzyl chloride and solvent. The resultant was dried in an oven to obtain the final product that is represented by the following Formula (IX):

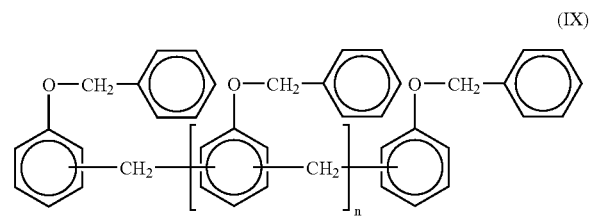

where n has an average value of 3.4.

(B$_3$) To compare with the phenol resin derivatives, a novolak phenol resin with a molecular weight of about 1000 was used, being represented by the following Formula (X):

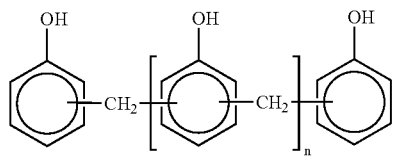

where n has an average value of 5.2.

(C) Phosphorous Compound ($C_1$) Triphenylphosphate (TPP) with a melting point of 48° C. was used.

($C_2$) Resorcinol diphosphate (RDP) (viscous liquid at room temperature) was used.

($C_3$) Triphenyl morpholido resorcinol diphosphate represented by the following Formula (XI) was used:

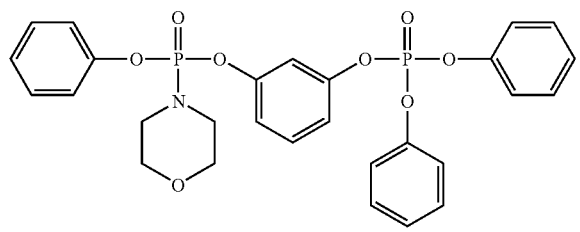

Examples 1–12

In Examples 1–5 and Comparative Examples 1–3, the compositions of the components are shown in Table 1. The resin compositions were extruded at 200~280° C. with a conventional twin screw extruder in pellets.

The resin pellets were dried at 80° C. for 3 hours, and molded into test specimens for measuring limited oxygen index (LOI) using a 6 oz injection molding machine at 220~280° C. The limited oxygen index was measured in accordance with ASTM D2863.

Comparative Examples 1–6

In Comparative Examples 1, 3 and 5, neither a phenol resin derivative nor a phenol resin was used, and in Comparative Examples 2, 4 and 6, a phenol resin ($B_3$) was used instead of a phenol resin derivative.

TABLE 1

| | Components | | | | | | | | | |
|---|---|---|---|---|---|---|---|---|---|---|
| | A | | | | B | | | C | | |
| | A1 | A2 | A3 | A4 | B1 | B2 | B3 | C1 | C2 | C3 | LOI |
| Examples | | | | | | | | | | | |
| 1 | 100 | — | — | — | 10 | — | — | 15 | — | — | 36 |
| 2 | 100 | — | — | — | 10 | — | — | — | 15 | — | 36 |
| 3 | 100 | — | — | — | 10 | — | — | — | — | 15 | 35 |
| 4 | 100 | — | — | — | — | 10 | — | 15 | — | — | 36 |
| 5 | 100 | — | — | — | — | 10 | — | — | 15 | — | 34 |
| 6 | 100 | — | — | — | — | 10 | — | — | — | 15 | 36 |
| 7 | — | 70 | 30 | — | 10 | — | — | 15 | — | — | 35 |
| 8 | — | 70 | 30 | — | — | 10 | — | 15 | — | — | 34 |

TABLE 1-continued

| | Components | | | | | | | | | |
|---|---|---|---|---|---|---|---|---|---|---|
| | A | | | | B | | | C | | |
| | A1 | A2 | A3 | A4 | B1 | B2 | B3 | C1 | C2 | C3 | LOI |
| 9 | — | 70 | 30 | — | 10 | — | — | — | 15 | — | 34 |
| 10 | — | 42 | 18 | 40 | 10 | — | — | 15 | — | — | 39 |
| 11 | — | 42 | 18 | 40 | — | 10 | — | 15 | — | — | 36 |
| 12 | — | 42 | 18 | 40 | — | 10 | — | — | — | 15 | 37 |
| Comp. Ex | | | | | | | | | | | |
| 1 | 100 | — | — | — | — | — | — | 15 | — | — | 21 |
| 2 | 100 | — | — | — | — | — | 10 | 15 | — | — | 27 |
| 3 | — | 70 | 30 | — | — | — | — | 15 | — | — | 23 |
| 4 | — | 70 | 30 | — | — | — | 10 | 15 | — | — | 29 |
| 5 | — | 42 | 18 | 40 | — | — | — | 15 | — | — | 26 |
| 6 | — | 42 | 18 | 40 | — | — | 10 | 15 | — | — | 30 |

Table 1 shows LOI of the resin compositions of Examples 1–12 and Comparative Examples 1–6. The higher LOI is, the more oxygen is required to burn the resin, which means that a higher LOI indicates good flame retardancy.

In Examples 1–12, a phenol resin derivative ($B_1$) or ($B_2$) was used. In Comparative Examples 1, 3 and 5, neither a phenol resin derivative nor a phenol resin was used, and in Comparative Examples 2, 4 and 6, a phenol resin ($B_3$) was used instead of a phenol resin derivative. The LOIs of Examples 1–12 are higher than those of Comparative Examples 1–6, showing better flame retardancy.

Accordingly, use of a phenol resin derivative with good char formability in a thermoplastic resin composition can provide good flame retardancy regardless of the base resin. Even if the base resin has no or poor char formability, the phenol resin derivative can provide good flame retardancy.

Examples of Compositions Containing Polyphenylene Ether Resin

The components to prepare flame retardant thermoplastic resin compositions which contain polyphenylene ether resin in Examples 1A~10A and Comparative Examples 1B~8B are as follows:

(A) Thermoplastic Resin (Base Resin)

($A_1$) High Impact Polystyrene (HIPS)

The high impact polystyrene was prepared through a conventional process, having 9% by weight of rubber content, 1.5 μm of average rubber particle size, and 220,000 of weight average molecular weight.

($A_2$) SAN Graft Copolymer 50 parts of butadiene rubber latex powder, 36 parts of styrene, 14 parts of acrylonitrile and 150 parts of deionized water were mixed. To the mixture, 1.0 parts of potassium oleate, 0.4 parts of cumenhydroperoxide, 0.2 parts of mercaptan-containing chain transfer agent, 0.4 parts of glucose, 0.01 parts of iron sulfate hydroxide and 0.3 parts of pyrophosphate sodium salt were added. The blend was kept at 75° C. for 5 hours to obtain ABS latex. To the ABS latex, 0.4 parts of sulfuric acid was added, coagulated and dried to obtain styrene-containing graft copolymer resin (g-ABS) in powder form.

(A₃) SAN Copolymer 75 parts of styrene, 25 parts of acrylonitrile, 120 parts of deionized water, 0.15 parts of azobisisobutylonitrile (AIBN) were blended. To the blend, 0.4 parts of tricalciumphosphate and 0.2 parts of mercaptan-containing chain transfer agent were added. The resultant solution was heated to 80? for 90 minutes and kept for 180 minutes. The resultant was washed, dehydrated and dried. Styrene-acrylonitrile copolymer (SAN) was obtained.

(A₄) Polycarbonate Resin

Polycarbonate of linear bisphenol-A type with a weight average molecular weight of 25,000 was used.

(B) Polyphenylene Ether Resin (PPE)

Poly(2,6-dimethyl-1,4-phenylene)ether by Japanese Asahi Co. (Product name: P-402) was used as PPE.

(C) Phenol Resin Derivative (C₁) The phenol resin derivative by Kukdo Chemical Co. of Korea (product name: YDCN-500-7P) was used, being represented by the following Formula (VIII):

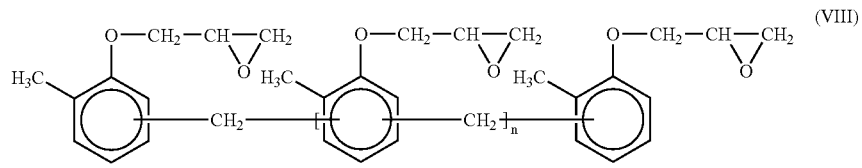

where n has an average value of 2.3.

(C₂) Novolak resin of 50 g with a softening point of 85° C., 200 g of benzyl chloride, and 150 g of isopropanol were dissolved in 20 ml of water, and the resulting solution was heated to 70° C. With agitation, 100 g of 20% NaOH was added to the solution over 1 hour. After reaction for more two hours, the solution was cooled to room temperature. The organic layer was separated from the water layer, and washed with distilled water several times. The separated organic layer was vacuum-distilled to remove benzyl chloride and solvent. The resultant was dried in an oven to obtain the final product that is represented by the following Formula (IX):

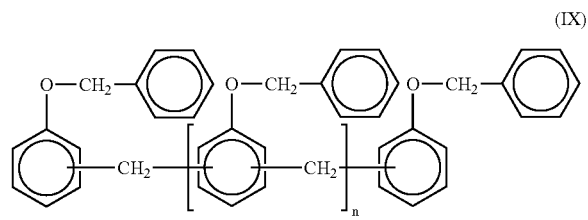

where n has an average value of 3.4.

(C₃) To compare with the phenol resin derivatives, a novolak phenol resin with a molecular weight of about 1000 was used, being represented by the following Formula (X):

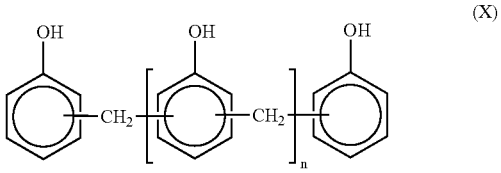

where n has an average value of 5.2.

(D) Phosphorous Compound (D₁) Triphenylphosphate (TPP) with a melting point of 48° C. was used.

(D₂) Resorcinol diphosphate (RDP) that is a viscous liquid at room temperature was used.

(D₃) Triphenyl morpholido resorcinol diphosphate represented by the following Formula (XI) was used:

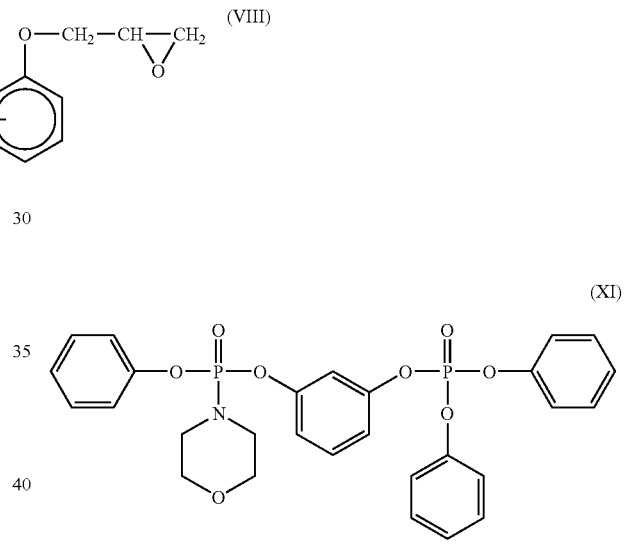

(E) Anti-Dripping Agent

Teflon (registered trademark) 7AJ by Mitsui Dupont company was used.

Examples 1A–5A and Comparative Examples 1B–3B

Use Of HIPS As Base Resin

HIPS was used as a base resin in Examples 1A–5A and Comparative Examples 1B–3B. The compositions of the components are shown in Table 1. The resin compositions were extruded at 250~280° C. with a conventional twin screw extruder in pellets.

The resin pellets were dried at 80° C. for 3 hours, and molded into test specimens for measuring flame retardancy and mechanical properties using a 6 oz injection molding machine at 220~280° C. The flame retardancy was measured in accordance with UL94VB. The test specimens have thickness of 3.2 mm and 1.6 mm.

As shown in Table 1, both PPE and a phenol resin derivative were used in Examples 1A–5A, PPE only was used in Comparative Example 1B, a phenol resin derivative was used in Comparative Example 2B, and both PPE and a conventional phenol resin were used in Comparative Example 3B.

As shown in Table 2, the resin compositions of Examples 6A–8A have better flame retardancy than those of Comparative Examples 4B–6B. The resin composition of Compara-

TABLE 1

|     |        | Examples |     |     |     |     | Comp. Examples |      |      |
|-----|--------|------|------|------|------|------|------|------|------|
|     |        | 1A   | 2A   | 3A   | 4A   | 5A   | 1B   | 2B   | 3B   |
| (A) | $(A_1)$ | 100 | 100 | 100 | 100 | 100 | 100 | 100 | 100 |
| (B) |        | 15  | 15  | 15  | 15  | 15  | 30  | —   | 15  |
| (C) | $(C_1)$ | 15  | —   | 5   | 15  | 15  | —   | 30  | —   |
|     | $(C_2)$ | —   | 15  | —   | —   | —   | —   | —   | —   |
|     | $(C_3)$ | —   | —   | —   | —   | —   | —   | —   | 15  |
| (D) | $(D_1)$ | 12  | 12  | 10  | —   | —   | 12  | 12  | 12  |
|     | $(D_2)$ | —   | —   | —   | 12  | —   | —   | —   | —   |
|     | $(D_3)$ | —   | —   | —   | —   | 12  | —   | —   | —   |
| (E) |        | —   | —   | 0.15 | —  | —   | —   | —   | —   |
| UL94VB |     |     |     |     |     |     |     |     |     |
| 3.2 mm |     | V1  | V1  | V1  | V1  | V1  | V1  | fail | fail |
| 1.6 mm |     | V1  | V1  | V1  | V1  | V1  | fail | fail | fail |

As shown in Table 1, the resin compositions of Examples 1A–2A have better flame retardancy than those of Comparative Examples 1B–2B. The resin composition of Comparative Example 3B shows poor flame retardancy, in which a conventional phenol resin was used instead of a phenol resin derivative.

When an anti-dripping agent is used as in Example 3A, the amounts of phenol resin derivative and PPE can be reduced without deteriorating flame retardancy of the resin composition.

Examples 6A–8A and Comparative Examples 4B–6B

Use Of ABS As Base Resin

ABS resin was used as a base resin in Examples 6A–8A and Comparative Examples 4B–6B. The compositions of the components are shown in Table 2. Examples 6A–8A and Comparative Examples 4B–6B were conducted in the same manner as in Examples 1A–5A.

As shown in Table 2, both PPE and a phenol resin derivative were used in Examples 6A–8A, PPE only was used in Comparative Example 4B, a phenol resin derivative was used in Comparative Example 5B, and both PPE and a conventional phenol resin were used in Comparative Example 6B.

TABLE 2

|     |        | Examples |     |     | Comp. Examples |     |     |
|-----|--------|------|------|------|------|------|------|
|     |        | 6A   | 7A   | 8A   | 4B   | 5B   | 6B   |
| (A) | $(A_2)$ | 70  | 70  | 70  | 70  | 70  | 70  |
|     | $(A_3)$ | 30  | 30  | 30  | 30  | 30  | 30  |
| (B) |        | 20  | 20  | 15  | 30  | —   | 20  |
| (C) | $(C_1)$ | 10  | —   | 10  | —   | 30  | —   |
|     | $(C_2)$ | —   | 10  | —   | —   | —   | —   |
|     | $(C_3)$ | —   | —   | —   | —   | —   | 10  |
| (D) | $(D_1)$ | 12  | 12  | 12  | 12  | 12  | 12  |
| (E) |        | —   | —   | 0.15 | —  | —   | —   |
| UL94VB | (3.2 mm) | V1 | V1 | V1 | V1 | fail | V1 |
|        | (1.6 mm) | V1 | V1 | V1 | fail | fail | fail | tive Example 6B shows poor flame retardancy, in which a conventional phenol resin was used instead of a phenol resin derivative.

When an anti-dripping agent is used as in Example 8A, the amounts of phenol resin derivative and PPE can be reduced without deteriorating flame retardancy of the resin composition.

Examples 9A–10A and Comparative Examples 7B–8B

Use Of PC(polycarbonate)/ABS Alloy As Base Resin

PC/ABS resin was used as a base resin in Examples 9A–10A and Comparative Examples 7B–8B. The compositions of the components are shown in Table 3. Examples 9A–10A and Comparative Examples 7B–8B were conducted in the same manner as in Examples 1A–5A.

As shown in Table 3, both PPE and a phenol resin derivative were used in Examples 9A–10A, PPE only was used in Comparative Example 7B, and both PPE and a conventional phenol resin were used in Comparative Example 8B.

TABLE 3

|     |        | Examples |     | Comp. Examples |     |
|-----|--------|------|------|------|------|
|     |        | 9    | 10   | 7    | 8    |
| (A) | $(A_2)$ | 42  | 42  | 42  | 42  |
|     | $(A_3)$ | 18  | 18  | 18  | 18  |
|     | $(A_4)$ | 40  | 40  | 40  | 40  |
| (B) |        | 10  | 10  | 25  | 10  |
| (C) | $(C_1)$ | 15  | —   | —   | —   |
|     | $(C_2)$ | —   | 15  | —   | —   |
|     | $(C_3)$ | —   | —   | —   | 15  |
| (D) | $(D_1)$ | 12  | 12  | 12  | 12  |
| UL94VB | (3.2 mm) | V1 | V1 | fail | fail |
|        | (1.6 mm) | V1 | V1 | fail | fail |

PC/ABS resin with over 70% by weight of PC can easily obtain good flame retardancy. However, PC/ABS resin with a lower content of PC like in Table 3 (40% PC content) cannot obtain good flame retardancy. Examples 9A and 10A show that PC/ABS resins with a lower content of PC, 40% content, can obtain UL 94 V1 flame retardancy if both PPE and a phenol resin derivative are used.

The present invention can be carried out by an ordinary skilled person in the art. Many modifications and changes may be deemed to be with the scope of the present invention as defined in the following claims.

What is claimed is:

1. A flame retardant thermoplastic resin composition comprising:
   (A) 100 parts by weight of a thermoplastic resin as a base resin;
   (B) about 0.1~100 parts by weight of polyphenylene ether;
   (C) about 0.1~100 parts by weight of a phenol resin derivative represented by the following Formula I;

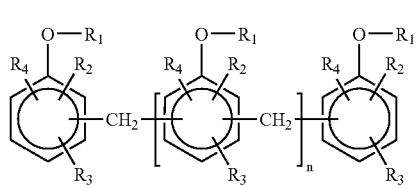

where $R_1$ is alkyl of $C_{1-34}$; aryl; alkyl-substituted aryl; O-, N-, P- or S-containing alkyl; O-, N-, P- or S-containing aryl; or O-, N-, P- or S-containing alkyl-substituted aryl; $R_2$, $R_3$, and $R_4$ are hydrogen, alkyl of $C_{1-34}$; aryl; alkyl-substituted aryl; O-, N-, P- or S-containing alkyl; O-, N-, P- or S-containing aryl; or O-, N-, P- or S-containing alkyl substituted aryl; and n is an integer of 1 to 10,000; and
   (D) about 0.1~50 parts by weight of a phosphoric acid ester morpholide compound.

2. The flame retardant thermoplastic resin composition as defined in claim 1, further comprising up to about 5.0 parts by weight of an anti-dripping agent based on 100 parts by weight of the base resin.

3. The flame retardant thermoplastic resin composition as defined in claim 2, wherein said anti-dripping agent is a fluoride resin.

4. The flame retardant thermoplastic resin composition as defined in claim 2, further comprising an additive comprising an impact modifier, a heat stabilizer, an oxidation inhibitor, a light stabilizer, talc, silica, mica, glass fiber, an organic or inorganic pigment and/or dye up to about 50 parts by weight as per 100 parts by weight of the base resin.

5. The flame retardant thermoplastic resin composition as defined in claim 1, wherein said base resin is selected from the group consisting of polyacrylonitrile-butadiene-styrene copolymer (ABS resin), rubber modified polystyrene resin (HIPS), acrylonitrile-styrene-acrylate copolymer (ASA resin), methacrylate-butadiene-styrene copolymer (MBS resin), acrylonitrile-ethacrylate-styrene copolymer (AES resin), polycarbonate (PC). polyethylene (PE), polypropylene (PP), polyethylene terephthalate (PET), polybutylene terephthalate (PBT), polyvinyl chloride (PVC), polymethyl metbacrylate (PMMA), polyamide (PA), and a copolymer thereof and an alloy thereof.

6. The flame retardant thermoplastic resin composition as defined in claim 1, wherein said phenol resin derivative is selected from the group consisting of o-cresol novolak epoxy resin, phenol epoxy resin and a mixture thereof.

7. A molded article prepared by the flame retardant thermoplastic resin composition of claim 1.

8. The flame retardant thermoplastic resin composition as defined in claim 1, wherein said phosphoric acid ester morpholide compound is represented by the following Formula (V):

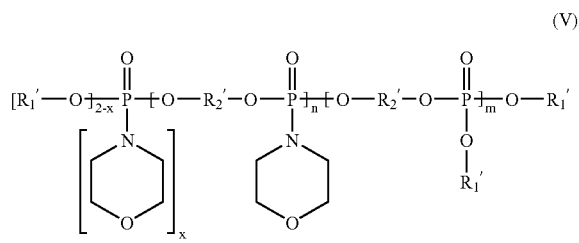

where $R'_1$ is a $C_{6-20}$ aryl group or an alkyl-substituted $C_{6-20}$ aryl group, $R'_2$ is a $C_{6-30}$ aryl group or an alkyl-substituted $C_{6-30}$ aryl group, x is 1 or 2, and n and m are number average degree of polymerization and n+m is 0 to 5.

9. A molded article prepared by the flame retardant thermoplastic resin composition of claim 8.

10. The flame retardant thermoplastic resin composition as defined in claim 8 wherein x is 1.

11. The flame retardant thermoplastic resin composition as defined in claim 8, where $R'_1$ is phenyl group or an alkyl-substituted phenyl group, where the alkyl is methyl, ethyl, isopropyl, t-butyl, isoamyl or t-amyl and $R'_2$ is a $C_{6-30}$ aryl group or an alkyl-substituted $C_{6-30}$ aryl group which is a derivative from resorcinol, hydroquinone, or bisphenol-A.

12. A flame retardant thermoplastic resin composition comprising:
   (A) 100 parts by weight of a thermoplastic resin as a base resin;
   (B) about 0.1~100 parts by weight of a phenol derivative represented by the following Formula:

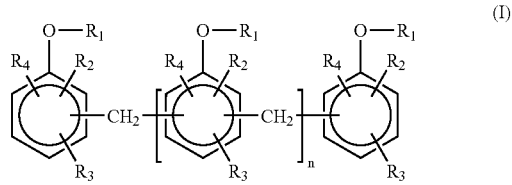

where $R_1$, is alkvl of $C_{1-34}$; alkyl; alkyl-substituted alkyl; O-, N-, P- or S-containing alkyl; O-, N-, P- or S-containing alkyl; or O-, N-, P- or S-containing alkyl-substitute alkyl; and $R_4$ are hydrogen, alkyl of $C_{1-34}$; aryl; alkyl-substituted aryl; O-, N-, P- or S-containing alkyl; O-, N-, P- or S-containing aryl; or O-, N-, P- or S-containing alkyl-substituted aryl; and n is an integer of 1 to 10,000; and about 1~50 parts by weight of phosphoric acid ester morpholide compound 1, represented by the following Formula:

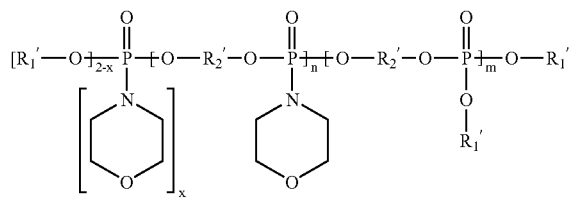 (V)

where R'$_1$ is a C$_{6-20}$ aryl group or an alkyl-substituted C$_{6-20}$ aryl group, R'$_2$ is a C$_{6-30}$ aryl group or an alkyl-substituted C$_{6-30}$ aryl group, x is 1 or 2, and n and m are number average degree of polymerization and n+m is 0 to 5.

13. A molded article prepared by the flame retardant thermoplastic resin composition of claim 12.

14. The flame retardant thermoplastic resin composition as defined in claim 12 wherein x is 1.

15. The flame retardant thermoplastic resin composition as defined in claim 12, where R'$_1$ is phenyl group or an alkyl-substituted phenyl group, where the alkyl is methyl, ethyl, isopropyl, t-butyl, isoamyl or t-amyl and R'$_2$ is a C$_{6-30}$ aryl group or an alkyl-substituted C$_{6-30}$ aryl group which is a derivative from resorcinol, hydroquinone, or bisphenol-A.

* * * * *